US005527300A

United States Patent [19]
Sauer

[11] Patent Number: 5,527,300
[45] Date of Patent: Jun. 18, 1996

[54] ABSORBENT ARTICLE WITH HIGH CAPACITY SURGE MANAGEMENT COMPONENT

[75] Inventor: Barbara O. Sauer, Fremont, Wis.

[73] Assignee: Kimberly-Clark Corporation, Neenah, Wis.

[21] Appl. No.: 299,711

[22] Filed: Aug. 31, 1994

[51] Int. Cl.$^6$ .................................................. A61F 13/15
[52] U.S. Cl. .................. 604/378; 604/385.2; 604/835.1; 604/373
[58] Field of Search ............................. 604/385.2, 385.1, 604/378, 368, 373

[56] References Cited

U.S. PATENT DOCUMENTS

| | | | |
|---|---|---|---|
| 3,901,236 | 8/1975 | Assarsson et al. | 128/284 |
| 4,050,462 | 9/1977 | Woon et al. | 128/287 |
| 4,076,663 | 2/1978 | Masuda et al. | 260/17.4 GC |
| 4,286,082 | 8/1981 | Tsubakimoto et al. | 526/240 |
| 4,326,528 | 4/1982 | Ryan et al. | 128/287 |
| 4,585,448 | 4/1986 | Enloe | 604/378 |
| 4,663,220 | 5/1987 | Wisneski et al. | 428/221 |
| 4,699,823 | 10/1987 | Kellenberger et al. | 428/219 |
| 4,704,116 | 11/1987 | Enloe | 604/385 A |
| 4,917,682 | 4/1990 | Lancaster et al. | 604/385.2 |
| 5,028,224 | 7/1991 | Pieper et al. | 425/80.1 |
| 5,147,343 | 9/1992 | Kellenberger | 604/368 |
| 5,192,606 | 3/1993 | Proxmire et al. | 428/284 |
| 5,226,992 | 7/1993 | Morman | 156/62.4 |
| 5,248,309 | 9/1993 | Serbiak et al. | 604/368 |
| 5,366,452 | 11/1994 | Widlund et al. | 604/385.2 |
| 5,417,680 | 5/1995 | Kimura et al. | 604/385.2 |

FOREIGN PATENT DOCUMENTS

0217032A2  4/1987  European Pat. Off. .
0339461B1 11/1989  European Pat. Off. .

Primary Examiner—Randall L. Green
Assistant Examiner—David J. Cho
Attorney, Agent, or Firm—Paul Yee

[57] ABSTRACT

A distinctive absorbent article has laterally opposed side margins, a front waistband portion, a back waistband portion, and an intermediate portion which interconnects the front and back waistband portions. The article comprises a backsheet layer, and an absorbent retention portion superposed on the backsheet layer. A liquid permeable topsheet layer is superposed on the retention portion to sandwich the retention portion between the topsheet and backsheet layers. A leg elastic connects to each of the side margins of the article to provide elasticized, gathered leg openings. A liquid permeable surge management portion is located adjacent a major facing surface of the topsheet layer. The surge management portion has laterally opposed side edge regions thereof, longitudinally opposed end sections thereof, and an intermediate section which interconnects the end sections. An contracting mechanism is incorporated into the surge management portion, and is constructed to operate separately from the leg elastics. The contracting mechanism is configured to shorten a length dimension of the surge management portion, and an attaching mechanism secures selected portions of the contracted, shortened surge management portion to the article.

23 Claims, 5 Drawing Sheets

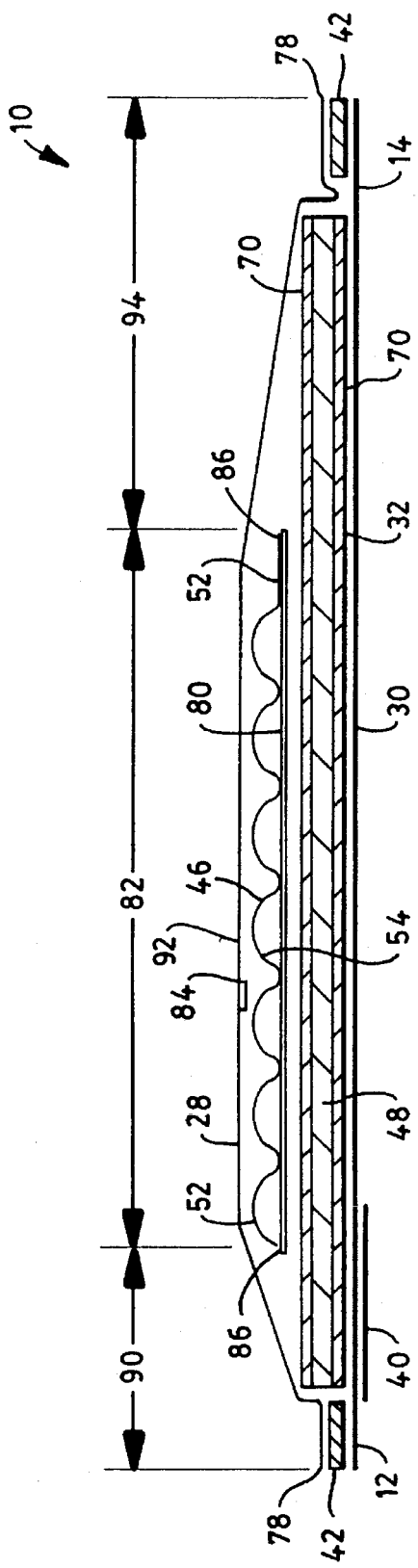
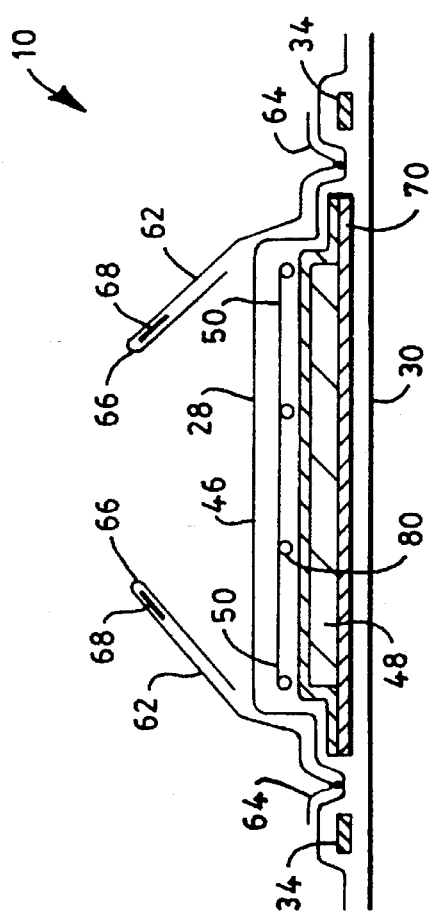

ABSORBENT ARTICLE WITH HIGH CAPACITY SURGE MANAGEMENT COMPONENT

FIELD OF THE INVENTION

The present invention relates to absorbent articles which are designed for the rapid uptake, distribution and retention of repeated liquid surges into the absorbent portion of the article. More particularly, the invention relates to an absorbent article having a surge management component which has been constructed and arranged to provide greater surge management capacity in a target region of the article.

BACKGROUND OF THE INVENTION

Desired performance objectives of personal care absorbent products include low leakage from the product and a dry feel to the wearer. However, absorbent products commonly fail before the total absorbent capacity of the product is utilized. An absorbent garment, such as an incontinence garment or disposable diaper, often leaks at the leg, top-front or top-back areas of the diaper. Leakage can occur due to a variety of shortcomings in the product, one being an insufficient rate of fluid uptake by the absorbent system, especially on the second or third liquid surges.

Attempts to alleviate leakage include providing physical barriers with elastic leg gathers and changing the amount or configuration of the absorbent material at the zone of the structure into which the liquid surges typically occur. To further reduce leakage, articles with elasticized leg gathers have further incorporated additional, elasticized containment or barrier flaps located at the interior of the structure. Absorbent gelling particles have also been included to increase the liquid holding capacity in various regions of the absorbent structure.

Absorbent articles have typically employed various types of absorbent pads composed of cellulosic fibers. Particular absorbent garments have been configured to control the distribution of absorbed liquids. For example, an absorbent article can have a liquid permeable transport layer which is located between a topsheet layer and an absorbent body. In other configurations, a conventional absorbent member can have fluid storage and acquisition zones composed of cellulosic fluff mixed with absorbent gelling particles; and may include a dual-layer absorbent core arrangement comprising a bottom fluff pad containing hydrogel particles, and a top fluff pad with little or no hydrogel particles.

Non-woven materials such as carded webs and spunbonded webs, have been used as the body-side liners in absorbent products. Specifically, very open, porous liner structures have been employed to allow liquid to pass through them rapidly, and help keep the body skin separated from the wetted absorbent pad underneath the liner. Some structures have incorporated zoned surfactant treatments in preselected areas of the liners to increase the wettability of the preselected regions and thereby control the amount of liquid wet-back onto a wearer's skin. In addition other layers of material, such as those constructed with thick, lofty fabric structures, have been interposed between the liner and absorbent pad for the purpose of reducing wet-back.

With conventional fluff-based absorbent structures, such as those discussed above, the cellulosic fibers, when wetted, can lose resiliency and collapse. As a result, the liquid uptake rate of the wetted structures may become too low to adequately accommodate subsequent, successive liquid surges. Where absorbent gelling particles are incorporated between the fibers to hold them apart, the gelling particles swell and do not release the absorbed fluid. Swelling of the particles can then diminish the void volume of the absorbent structure and reduce the ability of the structure to rapidly uptake liquid.

The addition of more absorbent material, such as secondary fluff pledgets, or absorbent gelling particles, has been employed to increase holding capacity. The desired rate of liquid intake within such arrangements, however, may not be sufficiently sustained during successive liquid surges.

Despite the development of absorbent structures of the types surveyed above, there remains a need for improved absorbent structures which can adequately reduce the incidence of leakage from absorbent products, such as disposable diapers. Conventional absorbent articles, such as those described above, have not been completely satisfactory when subjected to high loadings of liquids, such as urine. As a result, there is a need for an absorbent structure which can provide improved handling of liquid surges and can more effectively uptake and retain repeated loadings of liquid during use. There has also remained a continuing need for absorbent articles that can provide improved comfort and fit, and increased resistance to leakage.

BRIEF DESCRIPTION OF THE INVENTION

The present invention provides an absorbent article having laterally opposed side margins, a front waistband portion, a back waistband portion, and an intermediate portion which interconnects the front and back waistband portions. The article comprises a backsheet layer, and an absorbent retention portion superposed on the backsheet layer. A liquid permeable topsheet layer is superposed on the retention portion to sandwich the retention portion between the topsheet and backsheet layers. A leg elastic means connects to each of the side margins of the article to provide elasticized, gathered leg openings. A liquid permeable surge management portion is located adjacent a major facing surface of the topsheet layer. The surge management portion has laterally opposed side edge regions thereof, longitudinally opposed end sections thereof, and an intermediate section which interconnects the end sections. An contracting means is connected to the surge management portion and is constructed separate from the leg elastics. The contracting means is configured to shorten a length dimension of the surge management portion, and an attaching means secures the surge management portion to the article.

In particular aspects of the invention, the contracting means is configured to shorten a width dimension of the surge management portion. In other aspects, a first contracting means is configured to shorten a length dimension of the surge management portion, and a second contracting means is configured to shorten a width dimension of the surge management portion.

In the various aspects of the invention, a given quantity of surge management material can more effectively positioned and utilized. The surge management material can also be provided with increased basis weight and thickness, particularly in a selected target zone of an absorbent structure. As a result, an article of the invention can be constructed with less material at lower cost. The article can also more effectively handle sudden surges of liquid and provide reduced leakage.

BRIEF DESCRIPTION OF THE DRAWINGS

The invention will be more fully understood and further advantages will become apparent when reference is made to the following detailed description and accompanying drawings in which:

FIG. 3 representatively shows a schematic, lateral cross-sectional view taken through Section 3—3 of FIG. 1;

FIG. 4 representatively shows a schematic, longitudinal cross-sectional view taken through Section 4—4 of FIG. 1;

DETAILED DESCRIPTION OF THE INVENTION

The structures of the present invention will be described herein in relationship to their use in disposable absorbent articles, but it should be understood that potential uses of the structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants and the like.

Figure 1:
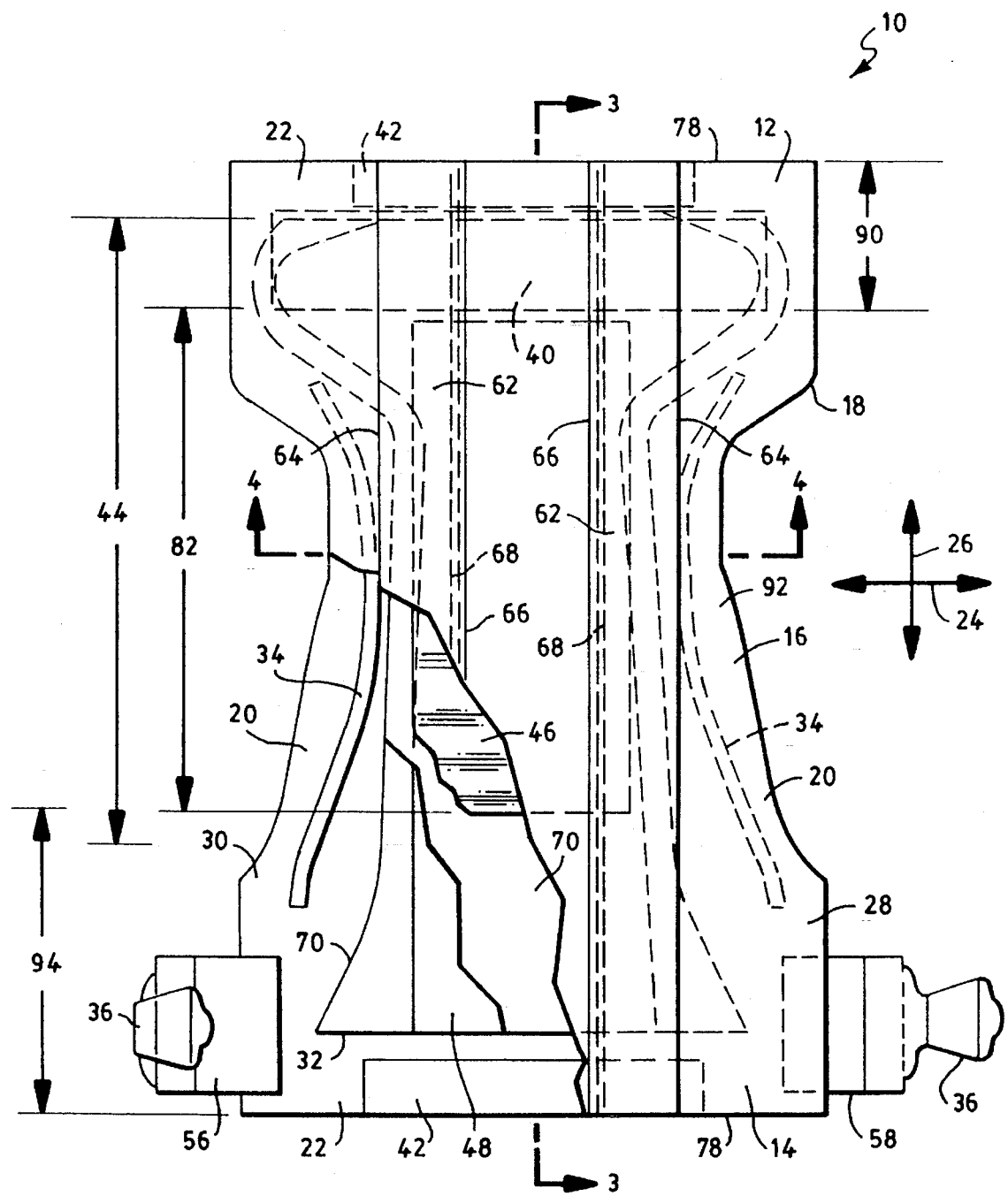
FIG. 1 representatively shows a partially cut-away, top view of an article of the invention.
Figure 2:
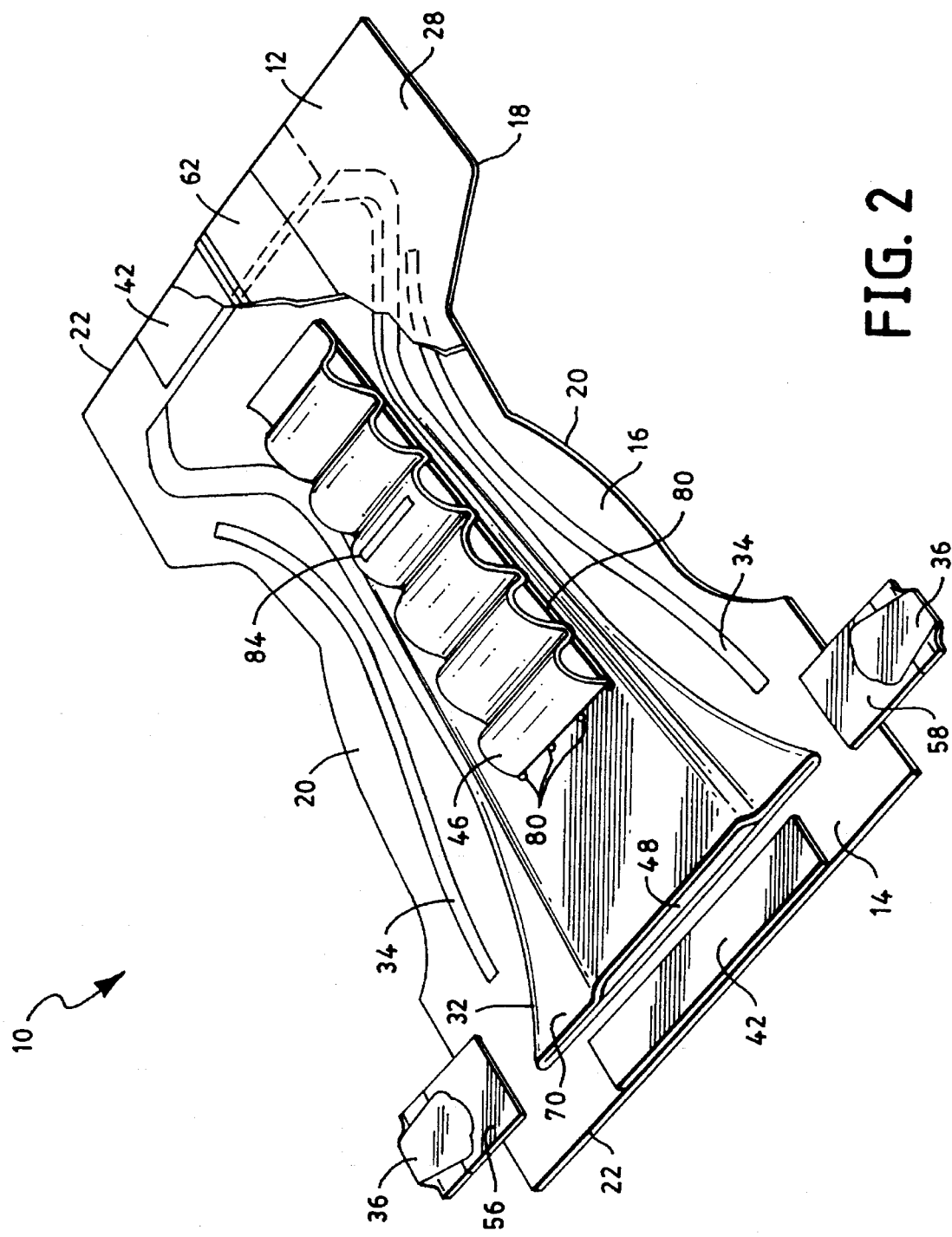
FIG. 2 representatively shows a partially cut-away, perspective view of the article of the invention having a longitudinally contracted surge management portion.

With reference to FIGS. 1 and 2, an absorbent article, such as diaper 10, has a cross-wise, lateral dimension 24 and a length-wise, longitudinal dimension 26. The representative diaper 10 has laterally opposed side margin 20, a front waistband portion 12, a back waistband portion 14, and an intermediate portion 16 which interconnects the front and back waistband portions. The article comprises a backsheet layer 30, and an absorbent body 32 which provides an absorbent retention portion 48 superposed on the backsheet layer 30. A liquid permeable topsheet layer 28 is superposed on the retention portion 48 to sandwich the retention portion between the topsheet and backsheet layers. The leg elastic 34 connects to each of the side margins 20 of the article to provide elasticized, gathered leg openings. A liquid permeable surge management portion 46 is located adjacent a major facing surface of the topsheet layer 28. The surge management portion has laterally opposed side edge regions 50 thereof (FIG. 4), longitudinally opposed end sections 52 thereof (FIG. 3) and an intermediate section 54 which interconnects the end sections 52. An contracting means is operably incorporated and connected to the surge management portion 46, and is constructed to operate substantially separately from the leg elastic members 34. The contracting means can be configured to retract and reduce a length dimension 82 of the surge management portion 46, and as shown in the illustrated embodiment, can be provided by one or more individual contractible members 80 which gather and foreshorten an appointed dimension, such as a length, of the surge management portion. An attaching means, such as adhesive bonds 84 (FIG. 3), secures the contracted and shortened surge management portion to the article.

FIG. 1 is a representative plan view of diaper 10 of the present invention in its substantially flat-out state (i.e., with all elastic induced gathering and contraction at the diaper leg bands and waistbands removed). Portions of the structure are partially cut away to more clearly show the interior construction of diaper 10, and the surface of the diaper which contacts the wearer is facing the viewer. In the shown embodiment, diaper 10 has a front waistband region 12, a back waistband region 14, an intermediate crotch region 16 which interconnects the front and rear waistband regions. The outer edges of the diaper define a periphery which includes longitudinally extending side edge margins 20 and laterally extending end edge margins 22. The side edge margins define leg openings for the diaper, and optionally, are curvilinear and contoured. The end edges define a waistband opening, and are shown as substantially straight, but optionally, may be curvilinear. The diaper additionally has a transversely extending, lateral width dimension 24 and a longitudinal, length dimension 26.

Diaper 10 typically includes a porous, liquid permeable topsheet 28; a substantially liquid impermeable backsheet 30; an absorbent structure 32, positioned between the topsheet and backsheet; a surge management portion 46; and elastic members such as leg elastics 34 and waist elastics 42. The surge management portion is positioned in liquid communication with the absorbent structure, and the absorbent structure includes a retention portion 48. Topsheet 28, backsheet 30, absorbent structure 32, surge management portion 46 and the elastic members 34 and 42 may be assembled in a variety of well-known diaper configurations. In addition, the diaper can include a system of containment flaps 62, and a system of side panel members 56 and 58.

Absorbent article structures suitable for use with the present invention are described in U.S. Pat. No. 5,192,606 to D. Proxmire et al. issued Mar. 9, 1993, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), the entire disclosure of which is hereby incorporated by reference in a manner that is consistent (not in contradiction) herewith. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the entire disclosure of which is hereby incorporated by reference in a manner that it is consistent herewith.

As representatively shown, topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter of the diaper 10, and in the illustrated embodiment, comprises laterally marginal end edge margins 22, and contoured longitudinally extending marginal side edge margins 20. The diaper 10 has front and back waistband regions 12 and 14, respectively, extending from the laterally extending end edges 22 of diaper periphery 18 toward the transverse center line of the diaper along a distance of from about 2 percent to about 10 percent of the overall length of diaper 10. The waistband regions comprise those upper portions of diaper 10, which when worn, wholly or partially cover or encircle the waist or mid-lower torso of the wearer. The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in the diaper or other disposable absorbent article.

Topsheet 28 presents a body-facing surface which is compliant, soft-feeling, and non-irritating to the wearer's skin. Further, topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% TRITON X-102 surfactant. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips employed to secure the containment flaps 62 onto topsheet 8 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The various configurations of the invention can include elasticized containment flaps 62, as representatively shown in FIGS. 1 and 4.

The shown configuration includes two containment flaps 62 which are connected to the bodyside surface of topsheet layer 28. Suitable constructions and arrangements for containment flaps 62 are described, for example, in U.S. Pat. No. 4,704,116 issued Nov. 3, 1987, to K. Enloe, the entire disclosure of which is hereby incorporated by reference in a manner that is consistent herewith. Other configurations of the containment flaps 62 are described in U.S. patent application Ser. No. 206,816 of R. Everett et al., filed Mar. 4, 1994 and entitled ABSORBENT ARTICLE HAVING AN IMPROVED SURGE MANAGEMENT (Attorney Docket No. 11,375), the entire disclosure of which is hereby incorporated by reference in a manner that is consistent herewith.

Such containment flaps can be attached to topsheet layer 28 along length-wise extending fixed regions, such as fixed edge regions 64, of the flaps. A movable edge region 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex LYCRA elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the barrier flap is connected to the flap elastics by partially doubling the flap material back upon itself by a limited amount which is sufficient to enclose flap elastics 68.

The containment flaps may, for example, be constructed of a fibrous material which is similar to the material comprising topsheet 28, or similar to the material comprising surge management portion 46. Other conventional materials, such as polymer films, may also be employed. In other aspects of the invention, barrier flaps 62 are constructed of a material which is permeable to gas, such as ambient air. Alternative configurations of the invention can include barrier flaps which are constructed of a material which is resistant to a passage of aqueous liquid, such as urine, therethrough. For example, barrier flaps 62 may be constructed of a spunbond-meltblown-spunbond (SMS) laminate material. In the illustrated embodiment, for example, the barrier flaps can be constructed of a SMS material having a basis weight of about 0.85 osy (about 28 gsm). The spunbond layers are composed of polypropylene fibers, and the meltblown layer is composed of meltblown polypropylene fibers.

In the various configurations of the invention, such as where the barrier flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated 31 Dec. 1968.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 can help prevent the exudates contained in absorbent structure 32 from wetting articles such as bedsheets and overgarments which contact diaper 10.

In particular embodiments of the invention, backsheet 30 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or non-woven fibrous web layer which has been totally or partially constructed or treated to impart the desired levels of liquid impermeability to selected regions that are adjacent or proximate the absorbent body. Backsheet 30 typically provides the outer cover of the article. Optionally, however, the article may comprise a separate outer cover member which is in addition to the backsheet.

Backsheet 30 may optionally be composed of a microporous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the attached marginal regions of topsheet 28 can include marginal end regions. The attached marginal end regions are located longitudinally outboard of the end edge regions of the retention portion 48 and/or surge management portion 46. Similarly, the attached marginal regions of backsheet 30 can include attached marginal end regions, which can be located longitudinally outboard of the end edge regions of the retention portion and/or surge management portion.

Elastic members 34 are disposed adjacent the periphery 18 of diaper 10 along each of the longitudinal side edges 20. The leg elastic members 34 can be connected to either or both of the topsheet and backsheet layers to provide elasticized side margins of the diaper article, and can be arranged to draw and hold diaper 10 against the legs of the wearer. Waist elastic members 42 may also be disposed adjacent either or both of the end edges of diaper 10 to provide elasticized waistbands.

Elastic members 34 and 42 are secured to diaper 10 in an elastically contractible condition so that in a normal, under strain configuration, the elastic members effectively contract against diaper 10. For example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather and shirr the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 and 42 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt or other type of adhesive.

In the illustrated embodiments of the invention, for example, leg elastic members 34 may comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. As representatively shown in FIG. 1, the curved elastics may have an inwardly bowed and outwardly bowed, reflex-type of curvature, and the length-wise center of the elastics may be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

An absorbent body, such as absorbent structure 32, is positioned between topsheet 28 and backsheet 30 to form diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

In the representatively shown embodiments, absorbent structure 32 includes a liquid-acquisition, target zone 44, and has a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. Target zone 44 encompasses the area where repeated liquid surges typically occur in absorbent structure 32. The particular location where liquid is discharged, such as during urination, can vary depending on the age and gender of the wearer. For example, male infants tend to urinate further toward the front end of the diaper. The female target zone is located closer to the center of the crotch. As a result, the shape and relative longitudinal placement of surge management portion 46 can be selected to best correspond with the actual target zone of either or both categories of wearers. Generally stated, the target zone is a section of absorbent structure 32 which is located in the front 60% of the length of the absorbent structure. With reference to the percentage of the total length of absorbent structure 32 measured into the absorbent structure from the front waistband edge thereof, the target zone may preferably comprise a region which begins at a line positioned approximately 10% of the absorbent structure length away from the front waistband edge and ends at approximately 60% of the absorbent structure length away from the front waistband edge.

The ear regions comprise portions which generally extend inwardly from the outermost lateral side edges of the absorbent structure toward its longitudinal center line. Thus, when the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied to provide desired performance characteristics.

In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance. Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly-(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled "ABSORBENT COMPOSITES AND ABSORBENT ARTICLES CONTAINING SAME" and filed on Sep. 11, 1991 (Attorney Docket No. 10174), the entire disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide a desired absorbency-under-load (AUL) value.

Superabsorbent materials having desired levels of AUL are described in detail in U.S. patent application Ser. No. 184,302 of S. Kellenberger and entitled "ABSORBENT PRODUCTS CONTAINING HYDROGELS WITH ABILITY TO SWELL AGAINST PRESSURE" (Attorney Docket No. 8786); European Patent Application EP 0 339 461A1, published Nov. 2, 1989; the entire disclosure of which is hereby incorporated by reference in a manner that is consistent with the present specification. An example of superabsorbent polymer material which can be suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desireable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–14 grams of fluff and more preferably includes about 10–12 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8.5 grams of superabsorbent polymer. Sufficient superabsorbent polymer is incorporated into retention portion 48 to provide an adequate total absorbent capacity of at least about 300 gm of urine. For example, a medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled "METHOD AND APPARATUS FOR INTERMITTENTLY DEPOSITING PARTICULATE MATERIAL IN A SUBSTRATE" and issued Jul. 2, 1991 (Attorney Docket No. 8761), the entire disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches, the narrowest portion of the crotch section has a width of about 3.5 inches and the back waistband region has a width of about 4.5 inches.

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles or other high-absorbency material in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

At least the bodyside layer of wrap sheet 70 has a pore distribution wherein no more than about 5 percent of the pores, as measured by Coulter porometry, are greater than about 50 micrometers in diameter. For example, the complete wrap sheet 70, or at least the bodyside layer of the wrap sheet, may comprise a meltblown web composed of meltblown polypropylene fibers having a fiber size of about 5 micrometers and arranged to form a basis weight within the range of about 8–20 gsm.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIGS. 1, 2 and 4. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outerside layers of absorbent wrap 70 extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

To provide the bonding between the bodyside and outerside portions of absorbent wrap 70, an adhesive, such as National Starch 72-3723 adhesive, can be printed onto appointed bonding areas of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. Retention portion 48 can then be placed between the bodyside and outerside portions of absorbent wrap 70, and the mating edges of the absorbent wrap portions can be bonded together to provide a generally complete peripheral seal along substantially the entire perimeter of the retention portion 48. In the illustrated embodiment, for example, the adhesive can be applied at an add-on rate of about 5 grams of solids per square meter of bonding to attach together the lapping edges of the bodyside and outerside portions of absorbent wrap 70.

With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

In the various embodiments of the invention, at least a major part of surge management portion 46 is located within target zone 44, and optionally, the surge management portion can have an areal extent which extends completely over target zone 44. Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in target zone 44, however, the particles can cause the structure to retain and hold unacceptably high amounts of the liquid. In addition, the transport of liquids away from target zone 44 to other sections of absorbent structure 32, particularly retention portion 48, can be undesirably impaired.

A capillary force differential created at the interface between the retention portion 48 and the material immediately adjacent the bodyside of the retention portion can improve the containment characteristics of absorbent structure 32. For example, if the surge management portion is composed of layer 46 positioned immediately adjacent to the retention portion, and if the surge layer is appropriately configured to provide and maintain a relatively lower capillary attraction, as compared to the capillary attraction exhibited by retention portion 48, then liquid surges occurring in target zone 44 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance 90 from a front waistband end edge of the retention portion 48, and can be spaced a different discrete distance 94 from a back waistband end edge of the retention portion.

Figure 5:
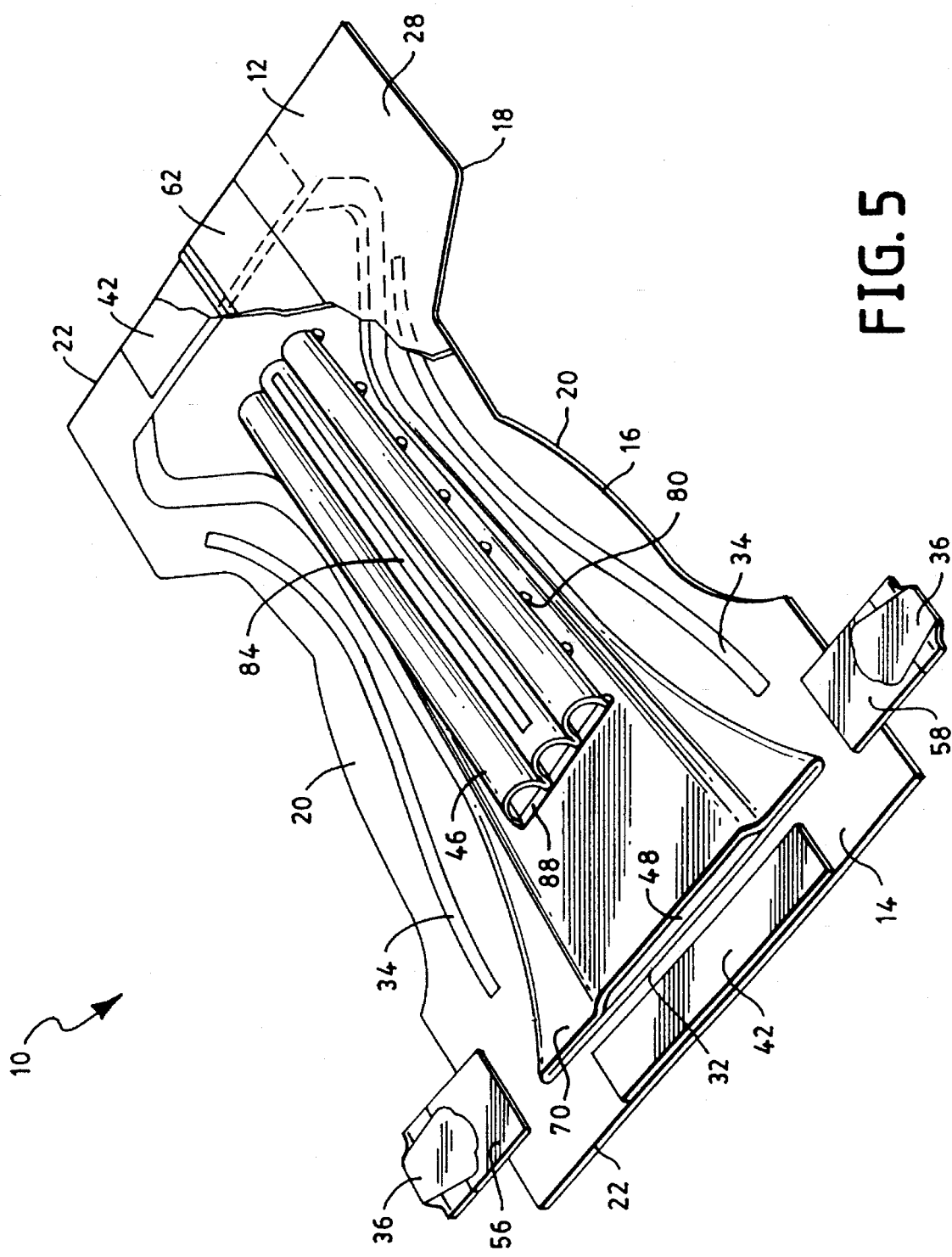
FIG. 5 representatively shows a partially cut-away, perspective view of the article of the invention having a laterally contracted surge management portion.
Figure 6:
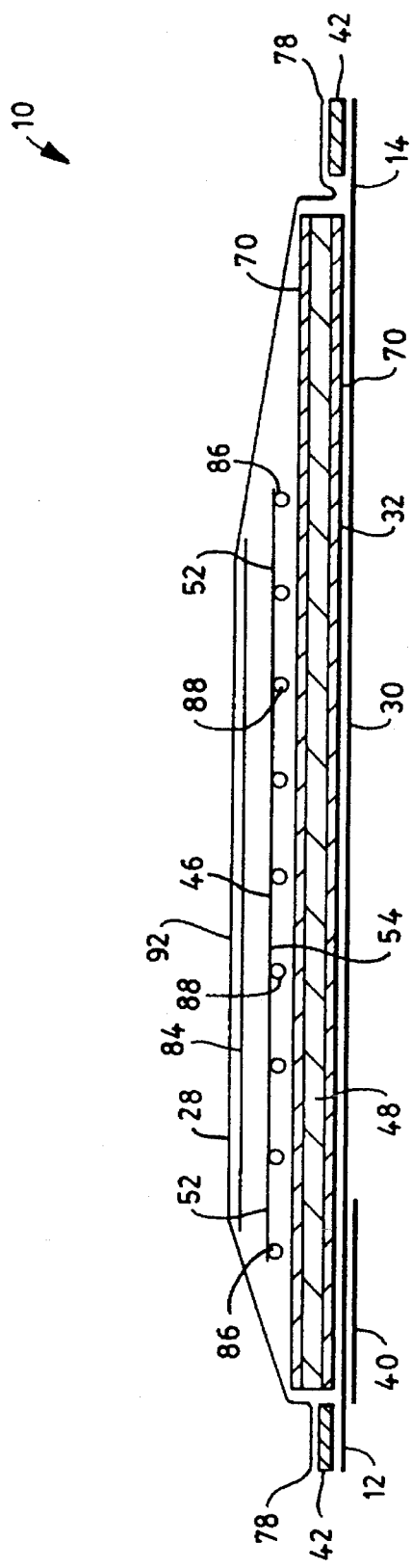
FIG. 6 representatively shows a schematic, lateral cross-sectional view taken through the article shown in FIG. 5.
Figure 7:
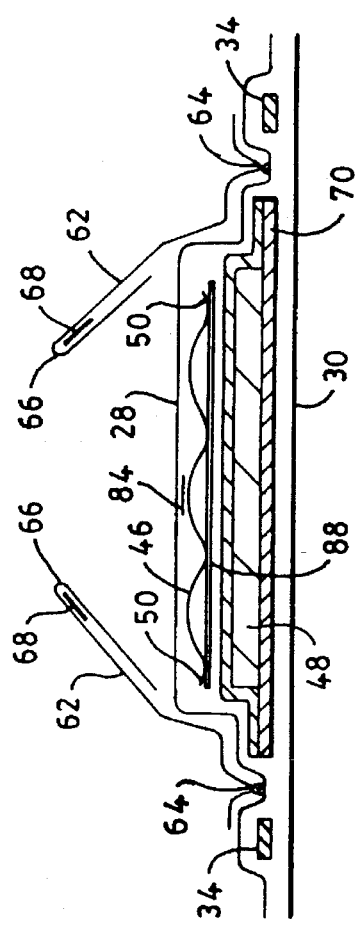
FIG. 7 representatively shows a schematic, longitudinal cross-sectional view taken through the article shown in FIG. 5.

With reference to FIGS. 2, 3 and 4, a contraction means, such as provided by at least one and desirably a plurality of contractible members 80, is operably connected to the surge management portion 46 to operably gather and shirr the surge management material, resulting in a higher loft and basis weight. In the illustrated embodiment, for example, the contractible members are located at each side edge region 50 of the surge management portion and are substantially aligned along the longitudinal direction 26. As representatively shown, the surge contractible members 80 can also be attached along a longitudinally-extending medial portion of the surge management portion which is positioned laterally inboard of the side regions 50. Alternative configurations (e.g. FIGS. 5, 6 and 7) of the surge management portion 46 can include at least one, and desirably a plurality of contractible members 88 which connect to the surge management material and are substantially aligned along the lateral, cross-direction 24. In the various constructions of the invention, the contractible members can be operably connected on top of, underneath, or sandwiched between two layers of surge material.

The surge contractible members 80 and 88 are constructed and arranged to operate substantially separately from the leg elastics 34 and waist elastics 42, and substantially do not operate to elasticize or gather the side or end margins, or the leg or waist openings of the diaper. Similarly, the leg and waist elastics 34 can be constructed and arranged to substantially avoid gathering the surge management portion.

The surge contractible members 80 and 88 can, for example, be composed of an elastomeric material which may be stretched prior to, during or after application to the surge management material, and then released to provide the appointed gathering and shirring. This elastic material may be in the form of strips, strands, ribbons, laminates, films, nonwovens, or foams, and may be of the chemical compositions found in natural rubber or synthetic elastomers, or combinations thereof. For example, the elastic material can be composed of synthetic thermoplastic elastomers, such as polyurethane elastomers, KRATON® elastomers (available from Shell Oil Company) or HYTREL® elastomers (available from E. I. DuPont de Nemours & Company), or thermoset urethanes.

The surge contractible members can be composed of materials which contract and foreshorten when subjected to an additional external treatment. For example, the contractible members may be composed of a heat-shrinkable material, which may be elastomeric or non-elastomeric. An example of a heat-shrinkable elastomer is PEBAX® (available from Atochem, Inc.) elastomer.

In particular aspects of the invention, the amount of shirring and contraction of the length and/or width of the surge management material can be at least about 10% of the original, uncontracted length and/or width of the surge management portion 46, and alternatively, can be at least about 40% of the original, uncontracted length and/or width of the surge management portion. In other aspects of the invention, the amount of shirring and contraction of the length and/or width of the surge management material can be not more than about 70% of the original, uncontracted length and/or width of the surge management portion 46, and alternatively, can be not more than about 60% of the original, uncontracted length and/or width of the surge management portion.

The contracted surge management portion is positioned in an operable, adjacent facing relation with a selected target zone 44 of the retention portion 48. The contracted surge may optionally extend beyond the target zone or may be shorter than the target zone along either or both of the lateral dimension 24 and the longitudinal dimension 26 of the article.

In particular aspects of the invention, the contracted length or width of the surge management portion 46 is not more than about 100% of the flat-out extended, ungathered length or width, respectively, of the retention portion 48. Alternatively, the contracted length or width of the surge management portion 46 can be not more than about 120% of the flat-out extended, ungathered length or width, respectively, of the retention portion, and optionally, may be not more than about 150% of the flat-out extended, ungathered length or width, respectively, of the retention portion.

In other aspects, the contracted length or width of the surge management portion 46 is at least about 20% of the flat-out extended, substantially ungathered length or width, respectively, of the retention portion 48. Alternatively, the contracted length or width of the surge management portion 46 can be at least about 40% of the Flat-out extended, ungathered length or width, respectively, of the retention portion, and optionally, may be at least about 70% of the flat-out extended, ungathered length or width, respectively, of the retention portion.

In the illustrated embodiment, the retention portion of the absorbent product lies below the contracted surge management portion adjacent the outwardly facing surface thereof. Alternatively, the retention portion 48 may be positioned generally adjacent a bodyside surface of the surge management portion 46. In still other configurations, the surge management portion may be located adjacent a bodyside surface of topsheet 28.

Where the surge management portion is contracted in the longitudinal direction 26 of the absorbent article, the surge portion is shortened lengthwise. As a result of the contraction, the surge material can have a corrugated appearance, with regular or irregular "hills and valleys" that are approximately aligned along the cross-direction 24 of the absorbent article. Alternatively, the surge management portion can be contracted along the cross-direction 24 of the article, and the surge portion can become narrower relative to its original cross-directional width. As a result of its contraction along the cross-direction, the surge can have a corrugated appearance wherein the regular or irregular "hills and valleys" can be approximately aligned along the lengthwise, longitudinal direction 26 of the article. Another configuration of the surge management portion can be constructed to have contraction along both the transverse and longitudinal directions 24 and 26. With this arrangement, the contracted surge can have a more random convoluted surface. In further aspects of the invention, the cross-directional and longitudinal contractions can be selectively limited to predetermined sections of the surge management portion 46. For example, either or both of the longitudinal end sections of the surge management portion can be contracted along length direction 26 and an intermediate section of the surge management portion can be contracted along the lateral direction 24. As a result, the length-wise extending hill regions in the intermediate section can more effectively block lateral, sideways movement of liquid past the article side margins at the article intermediate section 16, and the laterally extending hill regions in the end sections can more effectively block the movement of liquid past the article end margins at the article waistband sections 12 and/or 14.

The contraction of the surge management portion 46 can advantageously increase the effective basis weight, loft and thickness of the surge management material. In particular aspects of the invention, the loft or thickness of the surge material can be increased to at least about 120% of the uncontracted thickness of the surge material. Alternatively, the loft or thickness of the surge material can be increased to at least about 150% of the uncontracted thickness of the surge material, and can optionally be increased to about 250% of the uncontracted thickness of the surge material to provide improved benefits.

It should be appreciated that the amount of contractive force needed to shirr and gather the surge management material the desired amount, can depend on the rigidity and resistance of the surge material. For example, if an elasticized contractible member is used, the tension and/or elongation of the elastic member needs to be increased as the rigidity of the surge substrate increases, to obtain the same level of surge contraction. For example, two layers of surge management material can have a combined rigidity of 165 g, as measured prior to any interconnection or bonding between the layers. A suitable device for measuring the rigidity is a digital HANDLE-O-METER device, Model 211-5, available from the Thwing-Albert Instrument Company. The surge layers have an initial length of 10 inches, and require 4 strands of 740 decitex LYCRA® elastomer (available from E. I. DuPont de Nemours & Co.), spaced about 20 mm apart, sandwiched between the two layers, and elongated to 250%, to contract the surge material to approximately 50% of its original uncontracted length, to a final length of about 5 inches. In this example, the loft of the two layer surge composite increases about 186%, from 0.153 to 0.438 inches, as determined under a restraining pressure of 0.23 kPa (0.033 psi), such as measured using a 3" diameter circular platen weighing about 107 g. In the range of 150 to 300% elastic elongation, the surge contraction and loft increase, as occurring in this example, appeared to follow an asymptotic relationship, with a steep increase occurring at low elongations and with a leveling off occurring at about 250% elongation.

A suitable means of providing the contracted surge management portion is to connect an intermediate or medial section of the uncontracted surge management portion into the article at a selected location along the length or width of the retention portion 48 with an operable anchoring attachment 84. The resultant unanchored sections of the surge management portion 46 are substantially free to move relative to the remainder of the article. When the contractible members 80 and 88 are freed or otherwise activated, the non-anchored sections will retract toward the anchored location. For example, the contractible members may comprise previously stretched elastics which are held under tension and attached to the uncontracted surge management portion. When the tension is released, such as by cutting the stretched elastic, the non-anchored sections can retract toward the position of the anchor attachment 84. Alternatively, the contractible members may comprise a heat-shrinkable material which, upon heat activation, can retract toward the position of the anchor attachment.

Where the contractible members 80 are configured to gather the surge material along the longitudinal direction 26, the anchor attachment 84 can, for example, comprise a line or other region of attachment which extends laterally along a length-wise intermediate section of the surge management material. With reference to FIGS. 2 and 3, for example, a desired amount of differential contraction between the contracted surge management portion 46 and the gathered length of the article, can be provided by configuring anchor attachment 84 to operably secure a limited portion of an intermediate section 54 of the surge material to the intermediate section of diaper 10, such as an intermediate section 92 of topsheet 28. Accordingly, selected predetermined portions of the surge end sections 52 can be substantially unattached to topsheet 28 and can be substantially unattached to the diaper article. This configuration can operably holds the surge management portion 46 in the desired target zone 44 of the absorbent structure while also allowing the desired differential contraction between the contracted surge management portion and the other components of the article, such as the backsheet 30, the topsheet 28 and/or the retention portion 48. Accordingly, in particular aspects of the invention, the length or width of the contracted surge management portion can be less than the flat-out extended length or width, respectively, of the other components. In other aspects of the invention, the length or width of the contracted surge management portion can be less than the length or width, respectively, of the other components when the components are gathered by the operation of the leg elastics 34 and waist elastics 42.

Further aspects of the invention can include other advantageous dimensional relationships between the components of the article. In particular, the surge management portion 46 can have a flat-out extended, uncontracted length which is not less than a flat-out extended length of said article. For example, the surge management portion can have a flat-out extended length which is not less than a flat-out extended length of the backsheet 30, topsheet 28 and/or the retention portion 48 to provide improved benefits. Optionally, the surge management portion can have a flat-out extended length which is substantially equal to or smaller than a flat-out extended length of the backsheet 30, topsheet 28 and/or retention portion 48 to provide desired characteristics. The shortened width of the surge management portion may be less than a flat-out width of the article.

The shown embodiment illustrates an interconnection between surge management portion 46 and topsheet 28. It should be readily apparent, however, that the anchor attachment 84 may be arranged to secure the selected limited portion of surge management portion 46 to another substantially fixed component of the article, such as the wrapsheet 70 of the absorbent body 32, to produce an equivalent operational result.

Where the contractible members 88 are configured to gather the surge material along the lateral cross-direction 24 (FIGS. 5 and 7), the anchor attachment 84 can comprise a line or other region of attachment which extends longitudinally at the cross-wise center or medial region of the uncontracted surge management portion. The anchor attachment secures the surge management portion to a medial section of a selected, substantially fixed component of the article, such as a medial section of topsheet 28. As a result, the non-anchored sections of the surge management portion on either side of the anchor region can retract toward the centerline.

In particular aspects of the invention, the positioning of the anchor attachment 84 can be employed to control the positioning of each longitudinal end edge of the contracted surge management portion. For example, if the anchoring point provided by the attachment 84 is relatively closer to the front end margin of the article, the back portion of the surge management material can contract a greater length than the front portion.

One may alternatively regulate the amount of contraction toward the anchor point by selectively controlling the rigidity of the surge material. For example, the material of surge management portion 46 can have a back portion positioned relatively closer to the article back waistband portion 14, and a front portion positioned relatively closer to the article front waistband portion 12. The back portion of the surge material can be constructed with a higher rigidity than the front portion by varying the material composition or adding stiffening members. As a result, where the same level of contractive force is applied to both the Front and back portions of the surge material, the back portion can contract a lesser distance than the front portion. Likewise, the gain in basis weight and loft for the back portion would be less than the front portion, compared to the uncontracted values.

If the contraction of the surge material is provided in the transverse cross-direction 24 of the article, the anchor attachment 84 is desirably located along a longitudinally extending line which is approximately centered between the article side margins. Where the contraction of the surge material occurs in the longitudinal direction 26 of the article, the anchor attachment 84 is desirably offset toward the front waistband edge of the article, particularly in articles configured for male wearers.

In particular aspects of the invention, the rear section of the surge management portion can be contracted away from the back waistband margin of the article by a back spacing distance 94 which is within the range of 10–50% of the overall length of the article, as determined when the backsheet 30 is flat-out extended and ungathered. In other aspects of the invention, the front section of the surge management portion can be contracted away from the front waistband margin of the article by a front spacing distance 90 which is within the range of 0–30% of the overall length of the article to provide improved benefits.

The surge management anchor attachment 84 can be provided by a variety of mechanisms, such as adhesive bonds, thermal bonds, infrared bonding, ultrasonic bonds, stitching or the like, as well as combinations thereof. The anchor attachment, can be a contact point, line, or region, as long as the area of the anchor attachment 84 is less than the area of the surge management portion 46. Desirably, the anchor area is not more than about 50% of the area of the uncontracted surge management portion.

Another technique for providing a contracted surge management portion is to attach a previously contracted surge management portion to the article. The contractive activation, and/or relaxation of the contractible members 84 or 88 can occur prior to the attachment of the surge management portion to the absorbent article. In this configuration of the invention, the area of anchor attachment 84 need not be smaller than the area of the surge management portion 46, and the surge management portion can be adhered or otherwise attached to the article along substantially the entirety of its contracted length or contracted width.

In further aspect of the invention, the surge management portion 46 can be integrally composed an elastomeric fabric material. The material can, for example, comprise a woven or nonwoven web which includes natural or synthetic fibers incorporates a component composed of an elastomeric material. The material may also comprise a laminate or composite which includes films, threads, fibers or strips composed of an elastomeric material, such as urethanes, rubbers, and thermoplastic or thermoset elastomers.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney Docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney Docket No. 11,387); the entire disclosures of which are hereby incorporated by reference in a manner that is consistent herewith.

In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

The structures of other suitable surge management portions are described in U.S. Pat. No. 5,192,606 of D. Proxmire et al. issued Mar. 9, 1993, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932); and in U.S. patent application Ser. No. 07/757,760; "THIN ABSORBENT ARTICLE HAVING RAPID UPTAKE OF LIQUID"; of W. Hanson et al. (Attorney Docket No. 9922).

The basis weight of surge portion 46 can be important for providing a total holding capacity which is adequate to temporarily retain the amount of liquid that is typically discharged by a wearer during a single surge/insult of liquid into the absorbent article. It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends. The surge management material employed with the present invention will be at least about 20 grams per square meter with no real upper limit, with the target range being from about 40 to about 68 grams per square meter.

To ensure rapid intake of liquid, the overall structure of the surge portion 46 should have hydrophilic tendencies. At least a portion of the fibers should have a contact angle less than 90 degrees. As a result, the fibrous nonwoven web will have sufficient hydrophilic tendencies when the web has a saturation capacity greater than 55 grams of 0.9% saline solution per gram of web.

Another important feature of the surge material employed with the present invention is its resiliency in both the wet and dry states. A unique feature of the surge material is the amount of liquid which the material is able to absorb upon rapid insult. In addition, once the liquid has been absorbed, the surge material does not readily collapse. Excessive collapse would be detrimental to the overall performance of the material in that the collapsing of the material would result in a reduced capacity for retaining liquid. Surge materials employed with the present invention should have compression resilience values in both the wet and dry states of at least about 60%.

The distinctive parameters within the surge management portion, such as the permeability, specific volume, porosity, and the ratio of surface area to void volume parameters can advantageously provide for a sufficiently rapid uptake of the liquid surges delivered onto the target zone, and also allow a controlled spreading of the liquid through the void volume of its structure to temporarily fill it. Over a relatively short period of time, the surge management portion can then be desorbed through the cooperative operation of the underlying or otherwise adjacent liquid retention portion.

Fastening means, such as tape tab fasteners 36, are typically applied to the back waistband region 14 of diaper 10 to provide a mechanism for holding the diaper on the wearer. Tape tab fasteners 36 can be any of those well known in the art, and are typically applied to the corners of diaper 10. For example, adhesive fasteners, mechanical fasteners, hook and loop fasteners, snaps, pins or buckles, may be used alone, or in combination. In the shown configuration, the fasteners are adhesive fasteners, which are constructed to releasably adhere to a landing zone patch 40 attached to the front waistband section of the diaper to provide a refastenable adhesive fastening system. More particularly, the fastener tabs 36 connect to associated, laterally outboard edge regions of the side panels 56 and 58 along an appointed factory-bond region of the tab fasteners. In the shown configuration, for example, side panel members 56 and 58 are separate members operably connected and attached to laterally opposed end sections of the back waistband portion of backsheet 30. In particular aspects of the invention, the fastener tabs can have a relatively wide user-bond section in combination with a relatively narrower intermediate section. The intermediate section is positioned between the user-bond and factory-bond sections of the fastener tab.

Articles which include elastomeric side panels and distinctively configured fasteners are described in U.S. patent application Ser. No. 168,615 of T. Roessler et al., entitled DYNAMIC FITTING DIAPER and filed Dec. 16, 1993 (Attorney Docket No. 10,961), the entire disclosure of which is hereby incorporated herein by reference in a manner that is consistent herewith. The fastening systems can include a stress beam member for distributing applied stresses the area of the side panel material, and can include fastening tabs which incorporate a necked down intermediate region in combination with a relatively wider, userbond section thereof. Techniques for forming the desired fastening systems are described in U.S. patent application Ser. No. 200,593 of T. Roessler et al., entitled METHOD FOR MAKING A FASTENING SYSTEM FOR A DYNAMIC FITTING DIAPER and filed Feb. 23, 1994 (Attorney Docket No. 11,186), the entire disclosure of which is hereby incorporated herein by reference in a manner that is consistent herewith.

The side panels can be composed of a substantially non-elastomeric material, such as polymer films, woven fabrics, nonwoven fabrics or the like, as well as combinations thereof. In particular aspects of the invention, the side panels are composed of a substantially elastomeric material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European patent application EP No. 0 110 010 published on Apr. 8, 1987 with the inventors listed as J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

Having described the invention in rather full detail, it will be readily apparent that various changes and modifications can be made without departing from the spirit of the invention. All of such changes and modifications are contemplated as being within the scope of the invention, as called for by the subjoined claims.

We claim:

1. An absorbent article having laterally opposed side margins, a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion to sandwich said retention portion between said topsheet and backsheet layers;

a leg elastic connected to each of said side margins of said article to provide elasticized, gathered leg openings;

a liquid permeable surge management portion located between said retention portion and said topsheet layer, said surge portion having laterally opposed side edge regions thereof, longitudinally opposed end sections thereof and an intermediate section which interconnects said end sections;

a contracting means connected to said surge management portion and constructed separate from said leg elastics, said contracting means configured to shorten a length dimension of said surge management portion; and attaching means for securing said surge management portion to said article, said attaching means configured to secure a portion of said intermediate section of said surge management portion to said article with said end sections of said surge management portion unattached to said article, thereby allowing a differential contraction in length between said surge management portion and said topsheet layer.

2. An absorbent article as recited in claim 1, wherein said shortened length of said surge management portion is less than a flat-out length of said article.

3. An absorbent article as recited in claim 2, wherein said surge management portion is positioned adjacent an outwardly facing surface of said topsheet layer.

4. An absorbent article as recited in claim 1, wherein said surge management portion has a flat-out extended, uncontracted length which is not less than a flat-out extended length of said article.

5. An absorbent article as recited in claim 1, wherein said surge management portion has a flat-out extended, uncontracted length which is not less than a flat-out extended length of said retention portion.

6. An absorbent article as recited in claim 1, wherein said surge management portion has a flat-out extended, uncontracted length which is smaller than a flat-out extended length of said article.

7. An absorbent article as recited in claim 1, wherein said surge management portion has a flat-out extended length which is smaller than a flat-out extended length of said retention portion.

8. An absorbent article as recited in claim 1, wherein each of said contracting means comprises at least one elastic member.

9. An absorbent article as recited in claim 1, wherein each of said contracting means comprises at least one heat-shrinkable member.

10. An absorbent article as recited in claim 1, wherein said surge management portion is a fabric web including a fibers constructed of an elastomeric material to thereby provide said contracting means.

11. An absorbent article as recited in claim 1, wherein said attaching means is located relatively closer to a front margin of said article, thereby allowing a back portion of said surge management portion to contract a greater length than a front portion of said surge management portion.

12. An absorbent article as recited in claim 1, wherein a back portion of said surge management portion has a higher rigidity than a front portion of said surge management portion, thereby allowing said back portion to contract a lesser distance than said front portion.

13. An absorbent article as recited in claim 1, wherein a back portion of said surge management portion has a higher dignity than a front portion of said surge management portion, thereby allowing a contraction of said surge management portion to provide said back portion with a lesser gain in basis weight and loft than said front portion.

14. An absorbent article having laterally opposed side margins, a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion to sandwich said retention portion between said topsheet and backsheet layers;

a leg elastic connected to each of said side margins of said article to provide elasticized, gathered leg openings;

a liquid permeable surge management portion located between said retention portion and said topsheet layer, said surge portion having laterally opposed side edge regions thereof, longitudinally opposed end sections thereof and an intermediate section which interconnects said end sections;

a laterally extending contracting means connected to said surge management portion and constructed separate from said leg elastics, said contracting means configured to shorten a width dimension of said surge management portion; and attaching means for securing said surge management portion to said article, said attaching means configured to attach a cross-wise medial region of said surge management portion to said article at an anchor region and configured to provide non-anchored sections of said surge management portion on either side of said anchor region, thereby allowing said non-anchored sections to retract toward a centerline of said surge management portion.

15. An absorbent article as recited in claim 14, wherein said shortened width of said surge management portion is less than a flat-out width of said article.

16. An absorbent article as recited in claim 15, wherein said surge management portion is positioned adjacent an outwardly facing surface of said topsheet layer.

17. An absorbent article as recited in claim 16, wherein a longitudinally extending medial section of said surge management portion is secured to a longitudinally extending, medial portion of said article.

18. An absorbent article as recited in claim 17, wherein each of said contracting means comprises at least one elastic member.

19. An absorbent article as recited in claim 17, wherein each of said contracting means comprises at least one heat-shrinkable member.

20. An absorbent article as recited in claim 17, wherein said surge management portion is a fabric web which includes fibers constructed of an elastomeric material to thereby provide said contracting means.

21. An absorbent article having laterally opposed side margins, a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion to sandwich said retention portion between said topsheet and backsheet layers;

a leg elastic connected to each of said side margins of said article to provide elasticized, gathered leg openings;

a liquid permeable surge management portion located adjacent a bodyside surface of said retention portion, between said retention portion and said topsheet layer, said surge portion having laterally opposed side edge regions thereof, longitudinally opposed end sections thereof and an intermediate section which interconnects said end sections;

a first contracting means connected to said surge management portion and constructed separate from said leg elastics, said contracting means configured to shorten a length dimension of said surge management portion;

a second, laterally extending contracting means connected to said surge management portion and constructed separate from said leg elastics, said contracting means configured to shorten a width dimension of said surge management portion; and attaching means for securing said surge management portion to said article, said attaching means configured to secure a portion of said intermediate section of said surge management to said article with said end sections of said surge management portion substantially unattached to said article, thereby allowing a differential contraction in length between said surge management portion and said topsheet layer, and said attaching means configured to attach a cross-wise medial region of said surge management portion to said article at an anchor region and configured to provide non-anchored sections of said surge management portion on either side of said anchor region, thereby allowing said second contracting means to retract said non-anchored sections toward a centerline of said surge management portion.

22. An absorbent article as recited in claim 21, wherein a back portion of said surge management portion has a higher dignity than a front portion of said surge management portion, thereby allowing said back portion to contract a lesser distance than said front portion.

23. An absorbent article as recited in claim 21, wherein a back portion of said surge management portion has a higher dignity than a front portion of said surge management portion, thereby allowing a contraction of said surge management portion to provide said back portion with a lesser gain in basis weight and loft than provided to said front portion.

* * * * *

UNITED STATES PATENT AND TRADEMARK OFFICE
CERTIFICATE OF CORRECTION

PATENT NO.  : 5,527,300
DATED       : June 18, 1996
INVENTOR(S) : Barbara O. Sauer It is certified that error appears in the above-identified patent and that said Letters Patent is hereby corrected as shown below:

On the title page, under item [56], U.S. Patent Documents, insert

-- 4,775,375    10/1988    Aledo    604/378--

Foreign Patent Documents, insert

-- 0 183668    6/1986    Europe
   0 321985    6/1989    Europe
   0 355740    2/1990    Europe
   0 426197    5/1991    Europe
   0 604731    7/1994    Europe
   91/11161    8/1991    World
   94/05243    3/1994    World
   0 563841    7/1987    Australia --

Signed and Sealed this

Thirty-first Day of December, 1996

Attest:

BRUCE LEHMAN

Attesting Officer    Commissioner of Patents and Trademarks